(12) United States Patent
Kizuka et al.

(10) Patent No.: US 12,102,534 B2
(45) Date of Patent: Oct. 1, 2024

(54) STABILIZER FOR A MEDICAL DELIVERY SYSTEM

(71) Applicant: EVALVE, INC., Santa Clara, CA (US)

(72) Inventors: Koji J. Kizuka, Redwood City, CA (US); Alexander C. Chu, Diamond Bar, CA (US); Richard Childs, San Francisco, CA (US); Dylan Van Hoven, San Carlos, CA (US); Gabriel Gonzales, Milpitas, CA (US)

(73) Assignee: EVALVE, INC., Santa Clara, CA (US)

( * ) Notice: Subject to any disclaimer, the term of this patent is extended or adjusted under 35 U.S.C. 154(b) by 612 days.

(21) Appl. No.: 17/090,167

(22) Filed: Nov. 5, 2020

(65) Prior Publication Data
US 2021/0128305 A1 May 6, 2021

Related U.S. Application Data

(60) Provisional application No. 62/931,687, filed on Nov. 6, 2019.

(51) Int. Cl.
*A61B 90/50* (2016.01)
*A61F 2/24* (2006.01)
*A61B 1/00* (2006.01)
*A61B 90/57* (2016.01)

(52) U.S. Cl.
CPC ............ *A61F 2/2466* (2013.01); *A61F 2/246* (2013.01); *A61B 1/00147* (2013.01); *A61B 90/50* (2016.02); *A61B 90/57* (2016.02)

(58) Field of Classification Search
CPC ....... A61B 1/0047; A61B 90/50; A61B 90/57; A61F 2/2466; A61M 25/01; A61M 25/0113; A61M 25/013; A61M 25/0136; A61M 25/02; A61M 2025/0175; A61M 2025/024; A61M 2025/028
See application file for complete search history.

(56) References Cited

U.S. PATENT DOCUMENTS

| | | | |
|---|---|---|---|
| 3,378,010 | A | 4/1968 | Codling, et al. |
| 3,874,388 | A | 4/1975 | King et al. |
| 4,007,743 | A | 2/1977 | Blake |
| 4,055,861 | A | 11/1977 | Carpentier et al. |

(Continued)

FOREIGN PATENT DOCUMENTS

| | | |
|---|---|---|
| CA | 2 296 317 C | 1/2009 |
| EP | 0 558 031 B1 | 9/1993 |

(Continued)

OTHER PUBLICATIONS

International Search Report mailed Feb. 18, 2021 in International Application No. PCT/US2020/059013.

*Primary Examiner* — Katherine M Rodjom
(74) *Attorney, Agent, or Firm* — SLEMAN & LUND LLP

(57) ABSTRACT

Stabilizer for a medical delivery system is provided, wherein the medical delivery system has at least two portions translatable relative each other. The stabilizer includes a base and a sled coupled to the base. The sled includes a distal arm including a distal attachment for receiving a first portion of the medical delivery system, and a proximal arm including a proximal attachment for receiving a second portion of the medical delivery system. The sled is translatable relative to the base and the proximal attachment is translatable relative to the proximal arm.

26 Claims, 11 Drawing Sheets

(56) References Cited

U.S. PATENT DOCUMENTS

| | | | |
|---|---|---|---|
| 4,327,736 A | 5/1982 | Inoue | |
| 4,340,091 A | 7/1982 | Skelton et al. | |
| 4,657,024 A | 4/1987 | Coneys | |
| 4,693,248 A | 9/1987 | Failla | |
| 4,716,886 A | 1/1988 | Schulman et al. | |
| 4,795,458 A | 1/1989 | Regan | |
| 4,809,695 A | 3/1989 | Gwathmey et al. | |
| 4,930,674 A | 6/1990 | Barak | |
| 5,002,562 A | 3/1991 | Oberlander | |
| 5,069,679 A | 12/1991 | Taheri | |
| 5,098,440 A | 3/1992 | Hillstead | |
| 5,125,895 A | 6/1992 | Buchbinder et al. | |
| 5,147,370 A | 9/1992 | McNamara et al. | |
| 5,171,259 A | 12/1992 | Inoue | |
| 5,222,963 A | 6/1993 | Brinkerhoff et al. | |
| 5,271,544 A | 12/1993 | Fox et al. | |
| 5,327,905 A | 7/1994 | Avitall | |
| 5,330,501 A | 7/1994 | Tovey et al. | |
| 5,334,217 A | 8/1994 | Das | |
| 5,363,861 A | 11/1994 | Edwards et al. | |
| 5,389,077 A | 2/1995 | Melinyshyn et al. | |
| 5,403,326 A | 4/1995 | Harrison et al. | |
| 5,425,744 A | 6/1995 | Fagan et al. | |
| 5,450,860 A | 9/1995 | O'Connor | |
| 5,452,837 A | 9/1995 | Williamson, IV et al. | |
| 5,456,400 A | 10/1995 | Shichman et al. | |
| 5,456,674 A | 10/1995 | Bos et al. | |
| 5,478,353 A | 12/1995 | Yoon | |
| 5,542,949 A | 8/1996 | Yoon | |
| 5,562,678 A | 10/1996 | Booker | |
| 5,601,224 A | 2/1997 | Bishop et al. | |
| 5,601,574 A | 2/1997 | Stefanchik et al. | |
| 5,607,462 A | 3/1997 | Imran | |
| 5,607,471 A | 3/1997 | Seguin et al. | |
| 5,609,598 A | 3/1997 | Laufer et al. | |
| 5,611,794 A | 3/1997 | Sauer et al. | |
| 5,636,634 A | 6/1997 | Kordis et al. | |
| 5,695,504 A | 12/1997 | Gifford, III et al. | |
| 5,713,911 A | 2/1998 | Racenet et al. | |
| 5,716,417 A | 2/1998 | Girard et al. | |
| 5,741,297 A | 4/1998 | Simon | |
| 5,755,778 A | 5/1998 | Kleshinski | |
| 5,782,239 A | 7/1998 | Webster, Jr. | |
| 5,797,960 A | 8/1998 | Stevens et al. | |
| 5,810,847 A | 9/1998 | Laufer et al. | |
| 5,814,097 A | 9/1998 | Sterman et al. | |
| 5,843,178 A | 12/1998 | Vanney et al. | |
| 5,849,019 A | 12/1998 | Yoon | |
| 5,855,601 A | 1/1999 | Bessler et al. | |
| 5,976,159 A | 11/1999 | Bolduc et al. | |
| 6,015,417 A | 1/2000 | Reynolds, Jr. | |
| 6,048,351 A | 4/2000 | Gordon et al. | |
| 6,079,414 A | 6/2000 | Roth | |
| 6,117,144 A | 9/2000 | Nobles et al. | |
| 6,120,496 A | 9/2000 | Whayne et al. | |
| 6,149,658 A | 11/2000 | Gardiner et al. | |
| 6,165,183 A | 12/2000 | Kuehn et al. | |
| 6,182,664 B1 | 2/2001 | Cosgrove | |
| 6,193,734 B1 | 2/2001 | Bolduc et al. | |
| 6,200,315 B1 | 3/2001 | Gaiser et al. | |
| 6,217,528 B1 | 4/2001 | Koblish et al. | |
| 6,269,819 B1 | 8/2001 | Oz et al. | |
| 6,290,674 B1 | 9/2001 | Roue et al. | |
| 6,312,447 B1 | 11/2001 | Grimes | |
| 6,332,880 B1 | 12/2001 | Yang et al. | |
| 6,346,074 B1 | 2/2002 | Roth | |
| 6,419,696 B1 | 7/2002 | Ortiz et al. | |
| 6,461,366 B1 | 10/2002 | Seguin | |
| 6,482,224 B1 | 11/2002 | Michler et al. | |
| 6,496,420 B2 | 12/2002 | Manning | |
| 6,544,215 B1 | 4/2003 | Bencini et al. | |
| 6,551,303 B1 | 4/2003 | Van Tassel et al. | |
| 6,575,971 B2 | 6/2003 | Hauck et al. | |
| 6,599,311 B1 | 7/2003 | Biggs et al. | |
| 6,626,930 B1 | 9/2003 | Allen et al. | |
| 6,629,534 B1 | 10/2003 | St. Goar et al. | |
| 6,669,687 B1 | 12/2003 | Saadat | |
| 6,695,866 B1 | 2/2004 | Kuehn et al. | |
| 6,719,767 B1 | 4/2004 | Kimblad | |
| 6,752,813 B2 | 6/2004 | Goldfarb et al. | |
| 6,770,083 B2 | 8/2004 | Seguin | |
| 6,797,002 B2 | 9/2004 | Spence et al. | |
| 6,837,867 B2 | 1/2005 | Kortelling | |
| 6,855,137 B2 | 2/2005 | Bon | |
| 6,875,224 B2 | 4/2005 | Grimes | |
| 6,908,481 B2 | 6/2005 | Cribier | |
| 6,926,730 B1 | 8/2005 | Nguyen et al. | |
| 7,011,669 B2 | 3/2006 | Kimblad | |
| 7,101,395 B2 | 9/2006 | Tremulis et al. | |
| 7,112,207 B2 | 9/2006 | Allen et al. | |
| 7,125,421 B2 | 10/2006 | Tremulis et al. | |
| 7,226,467 B2 | 6/2007 | Lucatero et al. | |
| 7,556,632 B2 | 7/2009 | Zadno | |
| 7,563,267 B2 | 7/2009 | Goldfarb et al. | |
| 7,569,062 B1 | 8/2009 | Kuehn et al. | |
| 7,604,646 B2 | 10/2009 | Goldfarb et al. | |
| 7,635,329 B2 | 12/2009 | Goldfarb et al. | |
| 7,655,015 B2 | 2/2010 | Goldfarb et al. | |
| 7,666,204 B2 | 2/2010 | Thornton et al. | |
| 7,736,388 B2 | 6/2010 | Goldfarb et al. | |
| 7,811,296 B2 | 10/2010 | Goldfarb et al. | |
| 7,972,323 B1 | 7/2011 | Bencini et al. | |
| 7,981,139 B2 | 7/2011 | Martin et al. | |
| 8,057,493 B2 | 11/2011 | Goldfarb et al. | |
| 8,062,313 B2 | 11/2011 | Kimblad | |
| 8,118,822 B2 | 2/2012 | Schaller et al. | |
| 8,216,230 B2 | 7/2012 | Hauck et al. | |
| 8,216,256 B2 | 7/2012 | Raschdorf, Jr. et al. | |
| 8,303,608 B2 | 11/2012 | Goldfarb et al. | |
| 8,500,761 B2 | 8/2013 | Goldfarb et al. | |
| 8,734,505 B2 | 5/2014 | Goldfarb et al. | |
| 8,740,920 B2 | 6/2014 | Goldfarb et al. | |
| 8,945,177 B2 | 2/2015 | Dell et al. | |
| 9,011,468 B2 | 4/2015 | Ketai et al. | |
| 9,510,829 B2 | 12/2016 | Goldfarb et al. | |
| 10,076,415 B1 | 9/2018 | Metchik et al. | |
| 10,105,222 B1 | 10/2018 | Metchik et al. | |
| 10,123,873 B1 | 11/2018 | Metchik et al. | |
| 10,130,475 B1 | 11/2018 | Metchik et al. | |
| 10,136,993 B1 | 11/2018 | Metchik et al. | |
| 10,159,570 B1 | 12/2018 | Metchik et al. | |
| 10,231,837 B1 | 3/2019 | Metchik et al. | |
| 10,238,493 B1 | 3/2019 | Metchik et al. | |
| 10,245,144 B1 | 4/2019 | Metchik et al. | |
| D847,983 S | 5/2019 | Ho et al. | |
| 10,314,586 B2 | 6/2019 | Greenberg et al. | |
| 10,413,408 B2 | 9/2019 | Krone et al. | |
| 10,507,109 B2 | 12/2019 | Metchik et al. | |
| 10,517,726 B2 | 12/2019 | Chau et al. | |
| 10,524,792 B2 | 1/2020 | Hernandez et al. | |
| 10,595,997 B2 | 3/2020 | Metchik et al. | |
| 10,646,342 B1 | 5/2020 | Marr et al. | |
| 10,779,837 B2 | 9/2020 | Lee et al. | |
| D902,403 S | 11/2020 | Marsot et al. | |
| 10,856,988 B2 | 12/2020 | McNiven et al. | |
| 2002/0013571 A1 | 1/2002 | Goldfarb et al. | |
| 2002/0183787 A1 | 12/2002 | Wahr et al. | |
| 2003/0069593 A1 | 4/2003 | Tremulis et al. | |
| 2003/0167071 A1 | 9/2003 | Martin et al. | |
| 2004/0034365 A1 | 2/2004 | Lentz et al. | |
| 2004/0044350 A1 | 3/2004 | Martin et al. | |
| 2005/0267493 A1 | 12/2005 | Schreck et al. | |
| 2007/0038293 A1 | 2/2007 | Goar St. et al. | |
| 2007/0239105 A1* | 10/2007 | Weitzner | A61M 25/10184 604/95.01 |
| 2010/0160825 A1 | 6/2010 | Parihar et al. | |
| 2017/0042546 A1 | 2/2017 | Goldfarb et al. | |
| 2017/0049455 A1 | 2/2017 | Seguin | |
| 2017/0100201 A1* | 4/2017 | Ho | A61B 90/50 |
| 2017/0100250 A1* | 4/2017 | Marsot | A61F 2/2466 |
| 2017/0239048 A1 | 8/2017 | Goldfarb et al. | |
| 2017/0265994 A1 | 9/2017 | Krone | |
| 2018/0021133 A1 | 1/2018 | Barbarino | |
| 2018/0036119 A1 | 2/2018 | Wei et al. | |

(56) References Cited

U.S. PATENT DOCUMENTS

| | | |
|---|---|---|
| 2018/0092661 A1 | 4/2018 | Prabhu |
| 2018/0146964 A1 | 5/2018 | Garcia et al. |
| 2018/0235657 A1 | 8/2018 | Abunassar |
| 2018/0242976 A1 | 8/2018 | Kizuka |
| 2018/0243086 A1 | 8/2018 | Barbarino et al. |
| 2018/0325671 A1 | 11/2018 | Abunassar et al. |
| 2018/0344460 A1 | 12/2018 | Wei |
| 2018/0353181 A1 | 12/2018 | Wei |
| 2018/0360457 A1 | 12/2018 | Ellis et al. |
| 2019/0053803 A1 | 2/2019 | Ketai et al. |
| 2019/0125536 A1 | 5/2019 | Prabhu et al. |
| 2019/0151041 A1 | 5/2019 | Ho et al. |
| 2019/0151089 A1 | 5/2019 | Wei |
| 2019/0159899 A1 | 5/2019 | Marsot et al. |
| 2019/0167197 A1 | 6/2019 | Abunassar et al. |
| 2019/0183571 A1 | 6/2019 | De Marchena |
| 2019/0209293 A1 | 7/2019 | Metchik et al. |
| 2019/0247187 A1 | 8/2019 | Kizuka |
| 2019/0274831 A1 | 9/2019 | Prabhu |
| 2019/0321597 A1 | 10/2019 | Van Hoven et al. |
| 2019/0343630 A1 | 11/2019 | Kizuka |
| 2019/0350702 A1 | 11/2019 | Hernandez |
| 2019/0350710 A1 | 11/2019 | Ketai et al. |
| 2019/0365536 A1 | 12/2019 | Prabhu |
| 2020/0000473 A1 | 1/2020 | Dell et al. |
| 2020/0060687 A1 | 2/2020 | Hernández et al. |
| 2020/0078173 A1 | 3/2020 | McNiven et al. |
| 2020/0113678 A1 | 4/2020 | McCann et al. |
| 2020/0121460 A1 | 4/2020 | Dale et al. |
| 2020/0121894 A1 | 4/2020 | Prabhu et al. |
| 2020/0187942 A1 | 6/2020 | Wei |
| 2020/0205829 A1 | 7/2020 | Wei |
| 2020/0245998 A1 | 8/2020 | Basude et al. |
| 2020/0261107 A1 | 8/2020 | Cohen |
| 2020/0281591 A1 | 9/2020 | Krone et al. |
| 2020/0323528 A1 | 10/2020 | Khairkhahan |
| 2020/0323549 A1 | 10/2020 | Goldfarb et al. |
| 2020/0323634 A1 | 10/2020 | Von Oepen et al. |
| 2020/0360018 A1 | 11/2020 | Dell et al. |
| 2020/0367871 A1 | 11/2020 | Van Hoven et al. |
| 2020/0405485 A1 * | 12/2020 | Rohl .................... A61F 2/2466 |

FOREIGN PATENT DOCUMENTS

| | | |
|---|---|---|
| EP | 1 383 448 B1 | 6/2008 |
| FR | 2 768 324 A1 | 3/1999 |
| FR | 2 768 325 B1 | 11/1999 |
| WO | WO 91/01689 A1 | 2/1991 |
| WO | WO 92/12690 A1 | 8/1992 |
| WO | WO 94/018893 A1 | 9/1994 |
| WO | WO 96/32882 A1 | 10/1996 |
| WO | WO 97/27807 A1 | 8/1997 |
| WO | WO 98/07375 A1 | 2/1998 |
| WO | WO 99/07354 A2 | 2/1999 |
| WO | WO 99/13777 A1 | 3/1999 |
| WO | WO 99/15223 A1 | 4/1999 |
| WO | WO 00/03759 A2 | 1/2000 |
| WO | WO 00/60995 A2 | 10/2000 |
| WO | WO 01/28432 A1 | 4/2001 |
| WO | WO 03/020179 A1 | 3/2003 |
| WO | WO 03/049619 A2 | 6/2003 |
| WO | WO 2015/057289 A1 | 4/2015 |
| WO | WO 2016/178722 A1 | 11/2016 |
| WO | WO 2018/093663 A1 | 5/2018 |

* cited by examiner

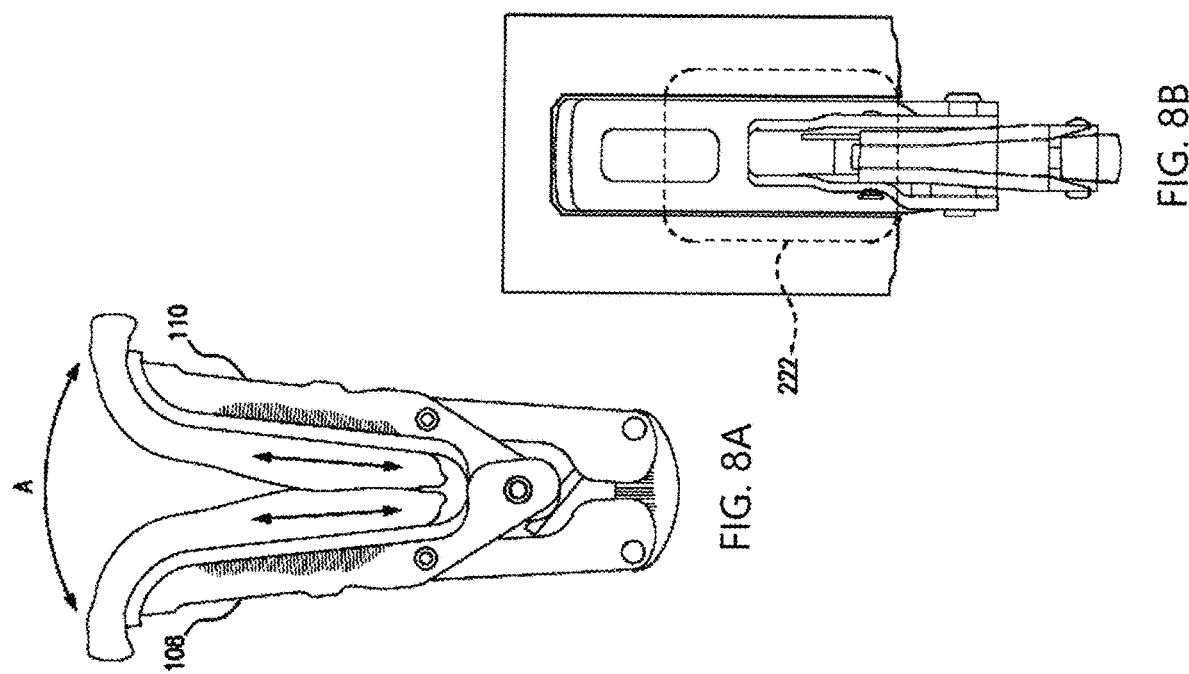

STABILIZER FOR A MEDICAL DELIVERY SYSTEM

CROSS-REFERENCE TO RELATED APPLICATIONS

This application claims priority to U.S. Provisional Application No. 62/931,687, filed Nov. 6, 2019, the full disclosure of which is incorporated herein by reference in its entirety.

BACKGROUND

Field of Disclosed Subject Matter

The disclosed subject matter is directed to medical devices for endovascular, percutaneous or minimally invasive surgical treatment of bodily tissues, such as tissue approximation or valve repair. More particularly, the present disclosure relates to repair of valves of the heart and venous valves.

Surgical repair of bodily tissues can involve tissue approximation and fastening of such tissues in the approximated arrangement. When repairing valves, tissue approximation includes coapting the leaflets of the valve in a therapeutic arrangement which can then be maintained by fastening or fixing the leaflets. Such coaptation can be used to treat regurgitation, which commonly occurs in the mitral valve and in the tricuspid valve.

Mitral valve regurgitation is characterized by retrograde flow from the left ventricle of the heart through an incompetent mitral valve into the left atrium. During a normal cycle of heart contraction (systole), the mitral valve acts as a check valve to prevent flow of oxygenated blood from the left ventricle back into the left atrium. Instead, as the left ventricle contracts the oxygenated blood is pumped from the left ventricle into the aorta through the aortic valve. Regurgitation of the mitral valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae connecting the leaflets to the papillary muscles, the papillary muscles, or the left ventricular wall can be damaged or otherwise dysfunctional. Commonly, the valve annulus can be damaged, dilated, or weakened, limiting the ability of the mitral valve to close adequately against the high pressures of the left ventricle.

Description of Related Art

Treatments for mitral valve regurgitation can involve valve replacement or repair including leaflet and annulus remodeling, the latter generally referred to as valve annuloplasty. Another technique for mitral valve repair, which can be referred to as the "bow-tie" or "edge-to-edge" technique, can involve suturing adjacent segments of the opposed valve leaflets together. Preferably, devices and systems for mitral valve repair can be utilized without open chest access, and, rather, can be capable of being performed endovascularly, i.e., delivering fixation devices (e.g., a valve repair clip) using delivery systems advanced to the heart from a point in the patient's vasculature remote from the heart. Furthermore, such delivery systems should allow for repositioning and optional removal of the fixation devices prior to fixation to provide proper placement. Stabilizer devices, such as a support frame, can be provided to support one or more portions of the delivery systems that remain external to the patient during repair procedures. Stabilizers are configured to maintain relative positions of various components of the delivery systems. During edge-to-edge repair procedures, however, the user (e.g., the medical professional performing the procedure) must be able to advance and retract various portions (or components) of the delivery system relative to one another. Typically, the user must manually lift and physically move the components relative to one another. The user also must be able to advance or retract the entire delivery system relative the patient's body. To do this, the user typically lifts and moves the entire system, including the stabilizer, relative the patient's body. As such, there remains a need for a stabilizer or system capable of simplified and controlled movement of related delivery systems and components. Such devices and systems likewise can be useful for repair of tissues in the body other than heart valves.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the systems and methods particularly pointed out in the written description and claims hereof, as well as from the appended drawings.

To achieve these and other advantages and in accordance with the purpose of the disclosed subject matter, as embodied and broadly described, the disclosed subject matter is directed to a stabilizer for a medical delivery system, as well as a system including the same.

In accordance with the disclosed subject matter, a stabilizer for a medical delivery system is provided, wherein the medical delivery system has at least two portions translatable relative each other. The stabilizer includes a base and a sled coupled to the base. The sled includes a distal arm including a distal attachment for receiving a first portion of the medical delivery system, and a proximal arm including a proximal attachment for receiving a second portion of the medical delivery system. The sled is translatable relative to the base and the proximal attachment is translatable relative to the proximal arm.

The stabilizer can include a sled drive mechanism coupled to the base and the sled. The sled drive mechanism can include a control knob to control movement of the sled drive mechanism to translate the sled relative the base. The sled drive mechanism can be a sled lead screw. The sled lead screw can be coupled to the sled by a threaded boss. Additionally or alternatively, the stabilizer can include an attachment drive mechanism coupled to the proximal arm and the proximal attachment. The attachment drive mechanism can include a control knob to control movement of the proximal attachment to translate the proximal attachment relative the proximal arm. The attachment drive mechanism can be an attachment lead screw. The attachment lead screw can be coupled to proximal arm by at least one threaded bearing block.

In accordance with the disclosed subject matter, the sled can be releasably coupled to the base. The base can include a flexible tab to releasably couple the base and the sled. The flexible tab can provide a distal stop to restrict translation of the sled relative the base.

At least one of the sled and the base can include indicia for position of the sled relative the base. The indicia can include a series of graduation marks disposed at equal intervals. The proximal arm can include a zero-reference marker for positioning the proximal attachment.

In accordance with the disclosed subject matter, a medical delivery system is provided. The medical delivery system can include an outer guide catheter, an inner guide catheter, an outer-guide-catheter handle, and inner-guide-catheter handle, and a stabilizer. The outer guide catheter has a distal end portion and a proximal end portion, and the inner guide catheter has a distal end portion and a proximal end portion. The outer-guide-catheter handle is coupled to the proximal end portion of the outer guide catheter and the inner-guide-catheter handle is coupled to the proximal end portion of the inner guide catheter. The stabilizer includes a base and a sled. The sled includes an outer-guide-catheter arm including an outer-guide-catheter attachment for receiving the outer-guide-catheter handle and an inner-guide-catheter arm including an inner-guide-catheter attachment for receiving the inner-guide-catheter handle. The sled is translatable relative to the base and the inner-guide-catheter attachment can be translatable relative to the inner-guide-catheter arm.

In accordance with the disclosed subject matter the medical delivery system can include a sled drive mechanism coupled to the base and the sled. The sled drive mechanism can include a control knob to control movement of the sled drive mechanism to translate the sled relative the base. The sled drive mechanism can be a sled lead screw. The sled lead screw can be coupled to the sled by a threaded boss. Additionally or alternatively, the medical delivery system can include an attachment drive mechanism coupled to the inner-guide-catheter arm and the inner-guide-catheter attachment. The attachment drive mechanism can include a control knob to control movement of the inner-guide-catheter attachment to translate the inner-guide-catheter attachment relative the inner-guide-catheter arm. The attachment drive mechanism can be an attachment lead screw. The attachment lead screw can be coupled to inner-guide-catheter arm by at least one threaded bearing block.

In accordance with the disclosed subject matter, the sled can be releasably coupled to the base. The base can include a flexible tab to releasably couple the base and the sled. The flexible tab can provide a distal stop to restrict translation of the sled relative the base.

At least one of the sled and the base can include indicia for position of the sled relative the base. The indicia can include a series of graduation marks disposed at equal intervals. The inner-guide-catheter arm can include a zero-reference marker for positioning the inner-guide-catheter attachment.

In accordance with the disclosed subject matter, the medical delivery system can include a delivery catheter having a distal end portion and a proximal end portion. The medical delivery system can include a fixation device coupled to the distal end portion of the delivery catheter. Additionally or alternatively the medical delivery system can include a delivery-catheter handle coupled to the proximal end portion of the delivery catheter.

BRIEF DESCRIPTION OF THE FIGURES

FIG. 8A is a front schematic view of the fixation device of FIG. 5 having leaflets captured therein.

FIG. 8B is a side view of the fixation device of FIG. 5 schematically depicting a contact patch area.

DETAILED DESCRIPTION

Figure 1:
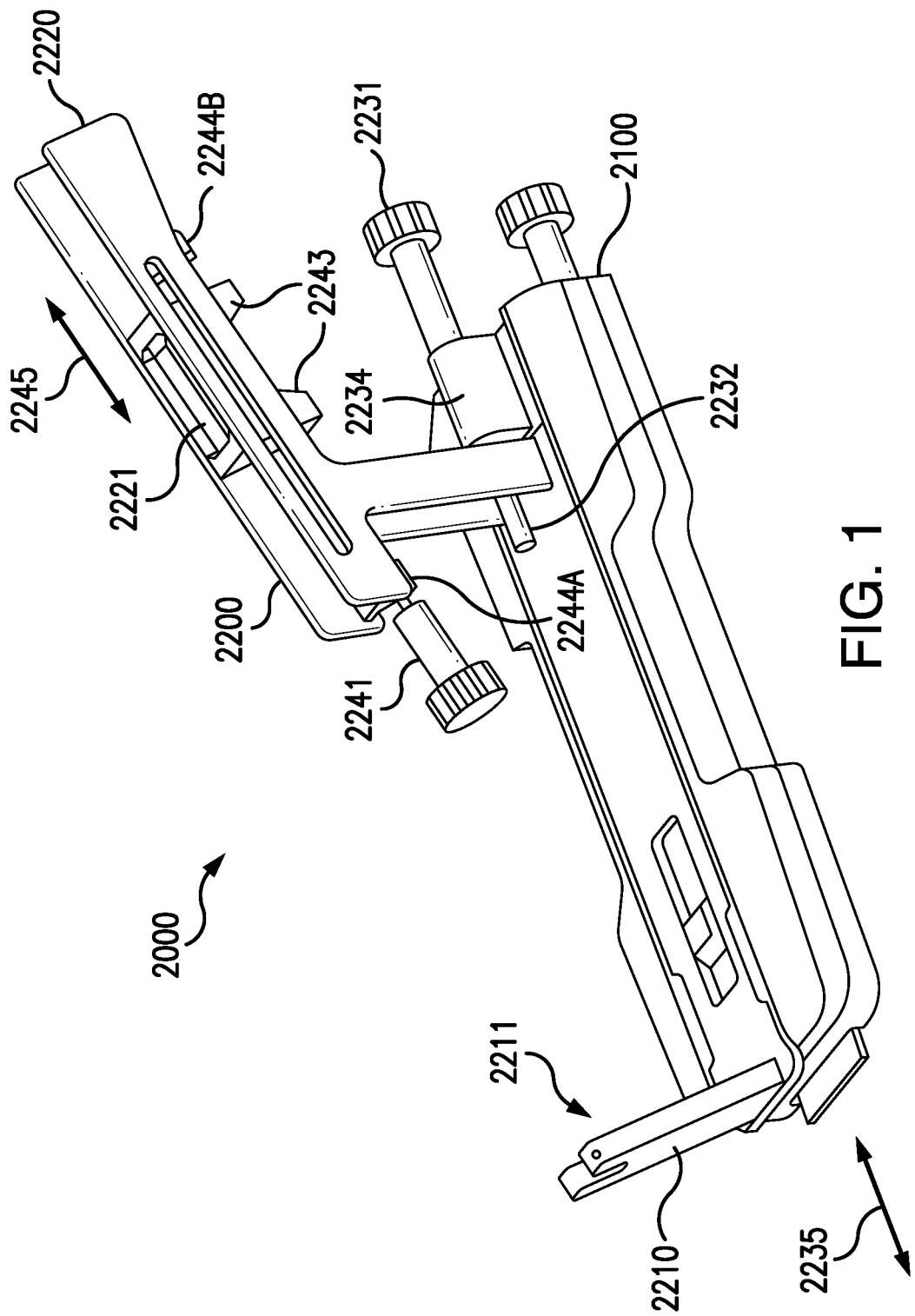
FIG. 1 is a perspective view of an exemplary embodiment of a stabilizer for use in accordance with the disclosed subject matter.

Reference will now be made in detail to the various exemplary embodiments of the disclosed subject matter, exemplary embodiments of which are illustrated in the accompanying drawings.

The stabilizer of the disclosed subject matter can be used for edge-to-edge transcatheter valve repair for patients having various conditions, including regurgitant mitral valves or tricuspid valves. Although described with respect to edge-to-edge repair, the stabilizer of the disclosed subject matter can be used with a wide variety of suitable transcatheter delivery systems. Transcatheter (e.g., trans-septal) edge-to-edge valve repair has been established using a fixation device, such as the MitraClip Transcatheter Mitral Valve Repair device. These fixation devices generally are configured to capture and secure opposing native leaflets using two types of leaflet contacting elements. The first element is a sub-valvular arm (also known as a distal element or fixation element) to contact the ventricular side of a native leaflet to be grasped. With the arm positioned underneath to stabilize the native leaflet in a beating heart, a second gripping element (also known as a proximal element) can be lowered or moved into contact with the atrial side of the native leaflet to capture the leaflet therebetween. Once each opposing leaflet is captured by a respective arm and gripper element, the fixation device can be closed by moving the arms toward a center of the fixation device such that the leaflets are brought into coaptation, which results in a reduction in valvular regurgitation during ventricular systole. Furthermore, a covering can be provided on the arms and/or gripper elements to facilitate tissue ingrowth with the captured leaflets. Such fixation devices can be delivered to the mitral valve using a delivery system. The delivery system can include multiple steerable catheter components that can be steered independently and moved relative one another to facilitate proper alignment of the fixation device with the leaflets prior to leaflet capture. Alignment can also be facilitated by moving the entire delivery system relative to the patient.

Additional details of exemplary fixation devices and delivery systems in accordance with the disclosed subject matter are set forth below. Furthermore, various patents and published applications disclose additional details of such fixation devices and delivery systems and related operations, for example, U.S. Pat. No. 7,226,467 to Lucatero et al., U.S. Pat. No. 7,563,267 to Goldfarb et al., U.S. Pat. No. 7,655,015 to Goldfarb et al., U.S. Pat. No. 7,736,388 to Goldfarb et al., U.S. Pat. No. 7,811,296 to Goldfarb et al., U.S. Pat. No. 8,057,493 to Goldfarb et al., U.S. Pat. No. 8,303,608 to Goldfarb et al., U.S. Pat. No. 8,500,761 to Goldfarb et al., U.S. Pat. No. 8,734,505 to Goldfarb et al., U.S. Pat. No. 8,740,920 to Goldfarb et al., U.S. Pat. No. 9,510,829 to Goldfarb et al., U.S. Pat. No. 7,635,329 to Goldfarb et al., U.S. Pat. No. 8,945,177 to Dell et al., U.S. Pat. No. 9,011,468 to Ketai et al., U.S. Patent Application Publication No. 2017/0042546 to Goldfarb et al., U.S. Patent Application Publication No. 2017/0239048 to Goldfarb et al., U.S. Patent Application Publication No. 2018/0325671 to Abunassar et al., the entirety of the contents of each of these patents and published applications is incorporated herein by reference.

Generally, and as set forth in greater detail below, the disclosed subject matter provided herein includes a stabilizer for a medical delivery system. The stabilizer of the disclosed subject matter can provide the user the ability to move various components of the medical delivery system as a whole without manually lifting and moving the structure. Also, the stabilizer of the disclosed subject matter provides the user with more precision and control when moving various portions of the delivery system relative to one another and when moving the entire delivery system relative to the patient.

In accordance with the disclosed subject matter, a stabilizer is provided including a base and a sled coupled to the base. The sled includes a distal arm including a distal attachment for receiving a first portion of the medical delivery system, and a proximal arm including a proximal attachment for receiving a second portion of the medical delivery system. The sled is translatable relative to the base and the proximal attachment is translatable relative to the proximal arm.

Referring now to FIGS. 1-4 for purpose of illustration and not limitation, a stabilizer 2000 for a medical delivery system (also referred to herein as "delivery system") is disclosed herein. The stabilizer 2000 includes a base 2100 and sled 2200. The base 2100 can have a planar shape for positioning on or against a flat surface, such as a table or benchtop. Alternatively, the base 2100 can be contoured to rest on a patient during use. The sled 2200 includes a distal arm 2210 which can include a distal attachment 2211 for receiving a first portion of a delivery system (for example, an outer guide catheter handle 1056, see FIGS. 10-11). The sled also includes a proximal arm 2220 which can include a proximal attachment 2221 for receiving a second portion of a delivery system (for example, an inner guide catheter handle 1057 and/or a delivery catheter handle 304, see FIGS. 9-11).

Distal attachment 2211 can include a yoke or similar structure which can include set screws and gripping elements or similar structure for receiving the first portion of the delivery system. The proximal attachment 2221 can be a block or similar structure, including a recess configured to receive the second portion of the delivery system. The proximal attachment 2221 can include set screws and gripping elements or similar structure for receiving the second portion of the delivery system.

Figure 2:
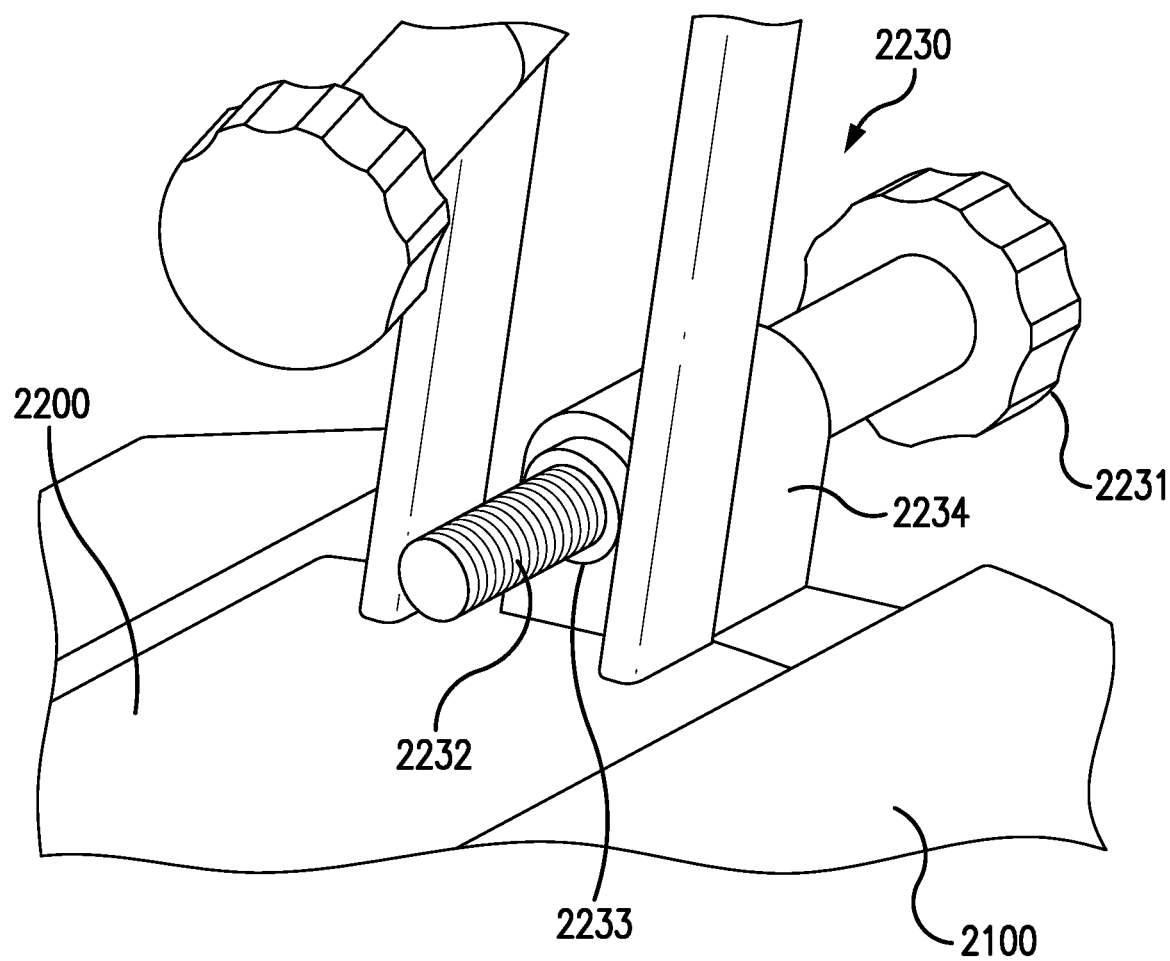
FIG. 2 is an enlarged detail view of a portion of the stabilizer of FIG. 1, depicting an exemplary sled drive mechanism.

The sled 2200 as disclosed herein is translatable relative to the base 2100. For example, the sled 2200 can be moved axially or longitudinally along the base 2100 within a guide or track or the like. Referring to FIGS. 1 and 2, for purpose of illustration and not limitation, the sled 2200 can include a sled drive mechanism 2230, which can be hydraulic, pneumatic, or otherwise mechanical. The sled drive mechanism 2230 can include a sled control knob 2231, however, sled drive mechanism 2230 can be controlled by any suitable control system, for example, a slide, trigger, handle, or digital control. As embodied herein, the sled drive mechanism 2230 can include a sled lead screw 2232 and the sled 2200 can include a threaded boss 2233, although the components can be reversed if desired. The threaded boss 2233 can be attached to the sled 2200, or the threaded boss 2233 can be unitary with the sled 2200. The sled lead screw 2232 can be received within the threaded boss 2233. The sled lead screw 2232 can be rotatably coupled to the base 2100, for example, by at least one bearing block 2234. When the sled control knob 2231 is rotated, the sled lead screw 2232 can rotate, which can translate the sled 2200 relative to the base 2100. In this manner, the sled 2232 can be translated distally or proximally along axis 2235 depending on the direction of rotation of the sled control knob 2231. Because the entire medical delivery system can be coupled to the sled 2200, as described further below, translation of the sled 2200 relative to the base 2100 can cause the medical delivery system to translate relative to the based, and thus patient.

Figure 3:
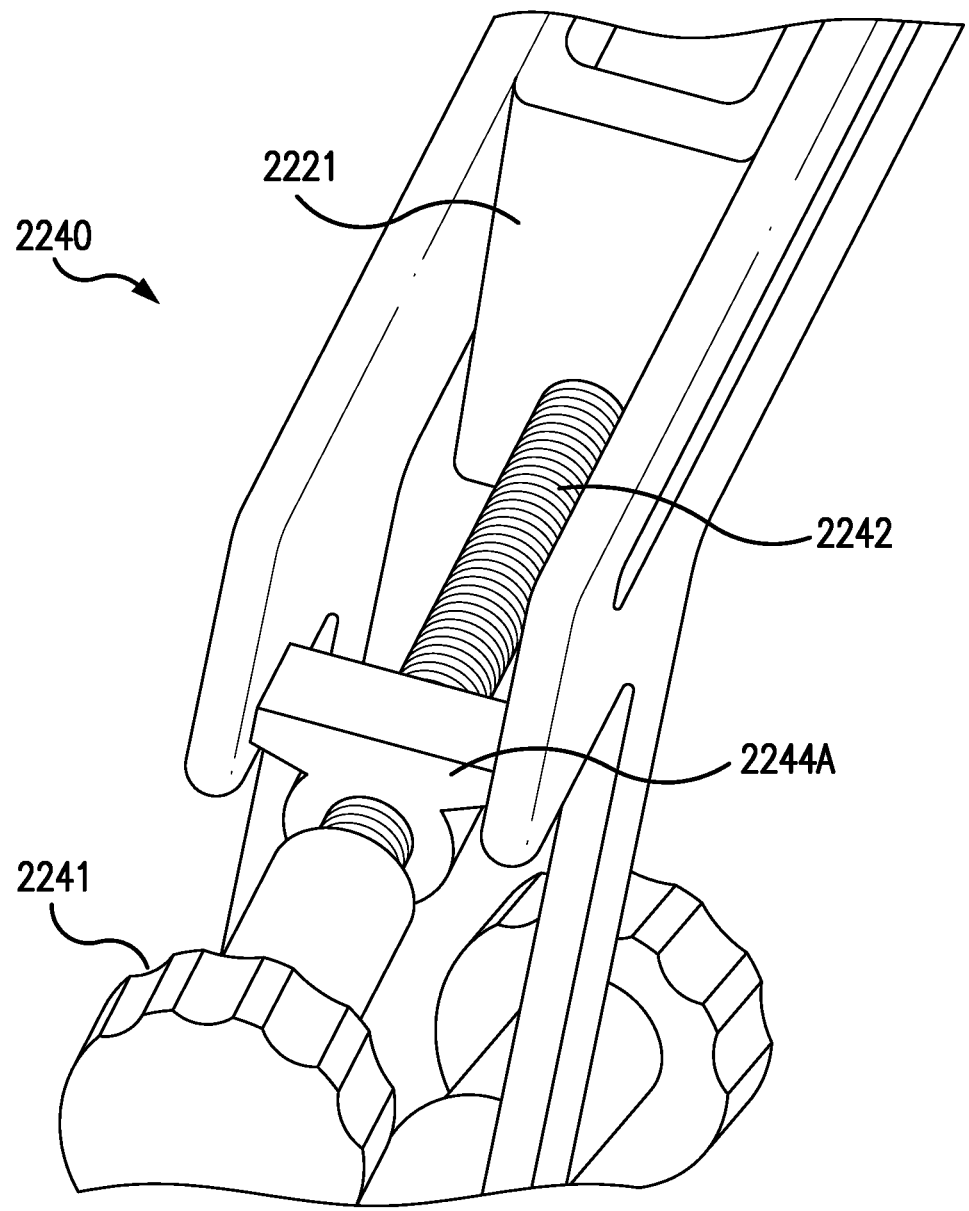
FIG. 3 is an enlarged detail view of a portion of the stabilizer of FIG. 1, depicting an exemplary attachment drive mechanism.

In accordance with the disclosed subject matter, the proximal attachment 2221 separately is translatable relative to the proximal arm 2220 (and therefore relative to the sled 2200 because the proximal arm 2220 and the sled 2200 are fixed relative one another). Referring to FIGS. 1 and 3, for purpose of illustration and not limitation, the proximal attachment 2221 can include an attachment drive mechanism 2240, which can be hydraulic, pneumatic, or otherwise mechanical. The attachment drive mechanism 2240 can include an attachment control knob 2241, however, attachment drive mechanism 2240 can be controlled by any suitable control system, for example, a slide, trigger, handle, or digital control. As embodied herein, the attachment drive mechanism 2240 can include an attachment lead screw 2242. The attachment lead screw 2242 can be rotatably coupled to the proximal arm 2220 (and therefore the sled), for example, by at least one threaded bearing block 2244. For example, and not limitation, the attachment lead screw 2242 embodied herein is attached to the proximal arm 2220 by two threaded bearing blocks 2244A, 2244B. The proximal attachment 2221 can receive the attachment lead screw 2242, for example, within a threaded portion 2243. When the attachment control knob 2241 is rotated, the attachment lead screw 2242 can rotate, which can translate the proximal attachment 2221 relative to the proximal arm 2220. In this manner, the proximal attachment 2221 can be translated distally or proximally along axis 2245 depending on the direction of rotation of the attachment control knob 2241. Because the second portion of the medical delivery system is attached to the proximal attachment 2221 (which moves relative to the sled 2200 when the attachment control knob 2241 is rotated) and the first portion of the medical delivery system is attached to the distal arm 2210 (which remains stationary relative to the sled 2200), translation of the proximal attachment 2221 relative to the sled 2200 can cause the second portion of the medical delivery system to translate relative to the first portion of the medical delivery system. For example, and as described further below, translation of the proximal attachment 2221 relative to the sled 2200 can move the inner guide catheter handle 1057 and the delivery catheter handle 304 relative to the outer guide catheter handle 1056.

Although this disclosure describes specific designs for the sled drive mechanism 2230 and attachment drive mechanism 2240, this disclosure contemplates any suitable drive mechanisms. For example, the sled drive mechanism 2230 and/or attachment drive mechanism 2240 can include worm gears, rack and pinion, pistons, solenoids or the like.

Figure 4:
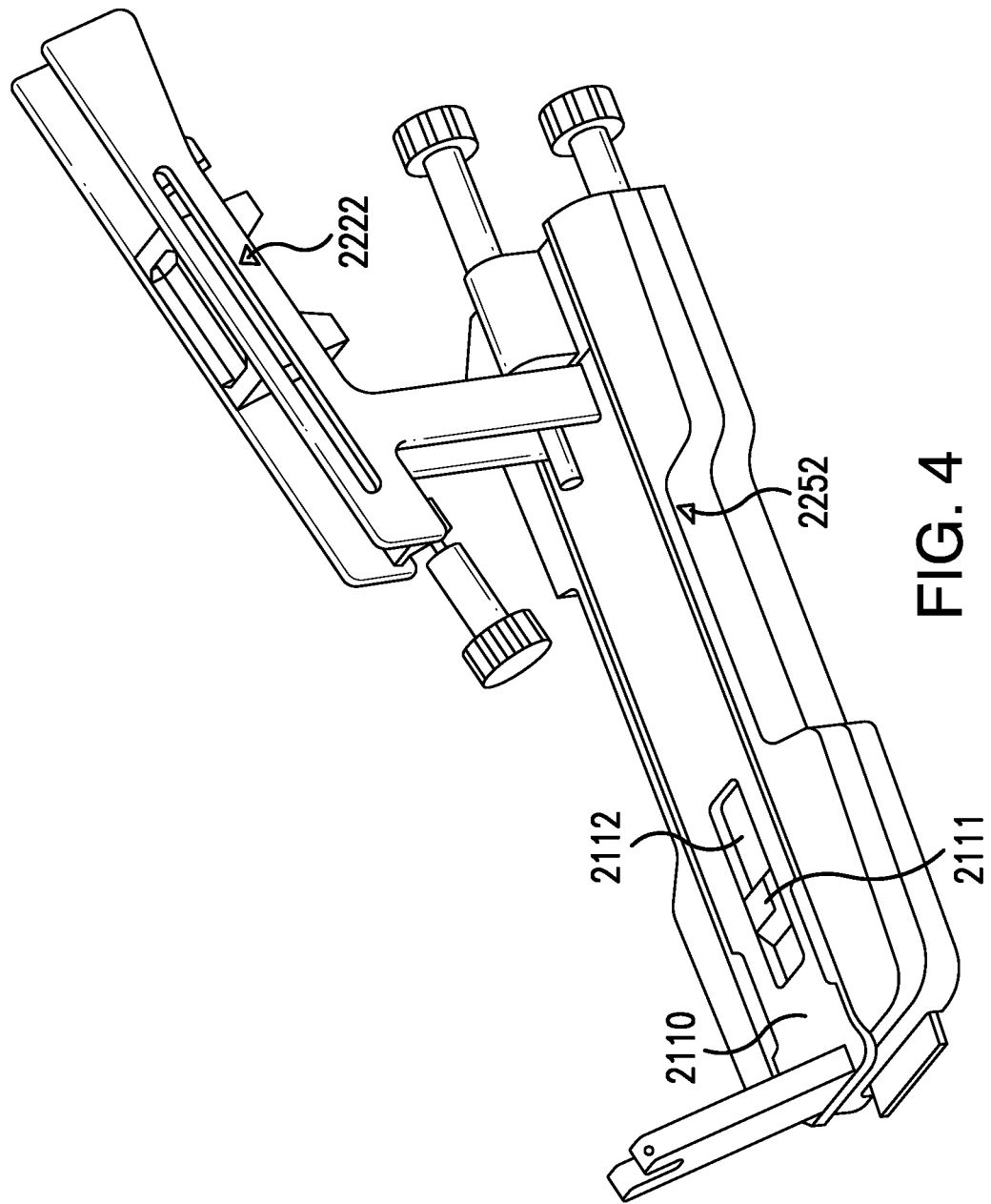
FIG. 4 is a perspective view of an exemplary embodiment of a stabilizer for use in accordance with the disclosed subject matter.

In accordance with the disclosed subject matter, at least one of the sled 2200 and the base 2100 can include indicia 2250 for positioning of the sled 2200 relative the base 2100. For example, the indicia 2250 can include a series of graduation marks 2251. The graduation marks can be disposed at equal intervals, such as 1 mm. The other of the sled 2200 and base 2100 can include an indicator arrow 2252 or the like. FIG. 4 shows, for purpose of illustration and not limitation, graduation marks 2251 disposed at 1 mm intervals on the sled 2200 and an indicator arrow 2252 disposed on the base 2100. The indicia thus can provide the operator with an indication of the relative movement or position of the delivery system relative the patient, for example, within a left atrium.

Additionally or alternatively, the proximal arm 2220 can include a zero-reference marker 2222. This can provide the user with a reference location for connecting the inner delivery catheter to the proximal attachment 2221. In accordance with the disclosed subject matter, the marker 2222 can assist the user in positioning the tip of the fixation device 104 relative to the outer guide catheter 1000. The user can then advance the proximal attachment 2221 using the attachment control knob 2241, which can provide enhanced control of translation of the inner guide catheter handle 1057 and the delivery catheter handle 304 relative to the outer guide catheter handle 1056.

In accordance with the disclosed subject matter, the stabilizer 2000 can be a reusable device. That is, the same stabilizer 2000 can be made of suitable materials to be sterilized and used for multiple surgical procedures. The base and 2100 and the sled 2200 can be releasably couple, which can allow for easier cleaning and sterilization between uses. Referring to FIG. 4, for purpose of illustration and not limitation, the base 2100 and the sled 2200 can be provided with a disassembly system 2110. The disassembly system 2110 can include a flexible tab 2111. For example, the flexible tab 2111 can be provided on the base 2100. The flexible tab 2111 can allow the sled 2200 to slide into the base, for example, by flexing downwardly. When the base 2100 and sled 2200 are coupled together, the flexible tab 2111 can return to a relaxed position and can provide a distal stop 2112 for translation of the sled 2200 in the distal direction. For disassembly, the flex tab 2111 can be manually flex downwardly, and the sled 2200 can slide distally off the base 2100.

Figure 5:
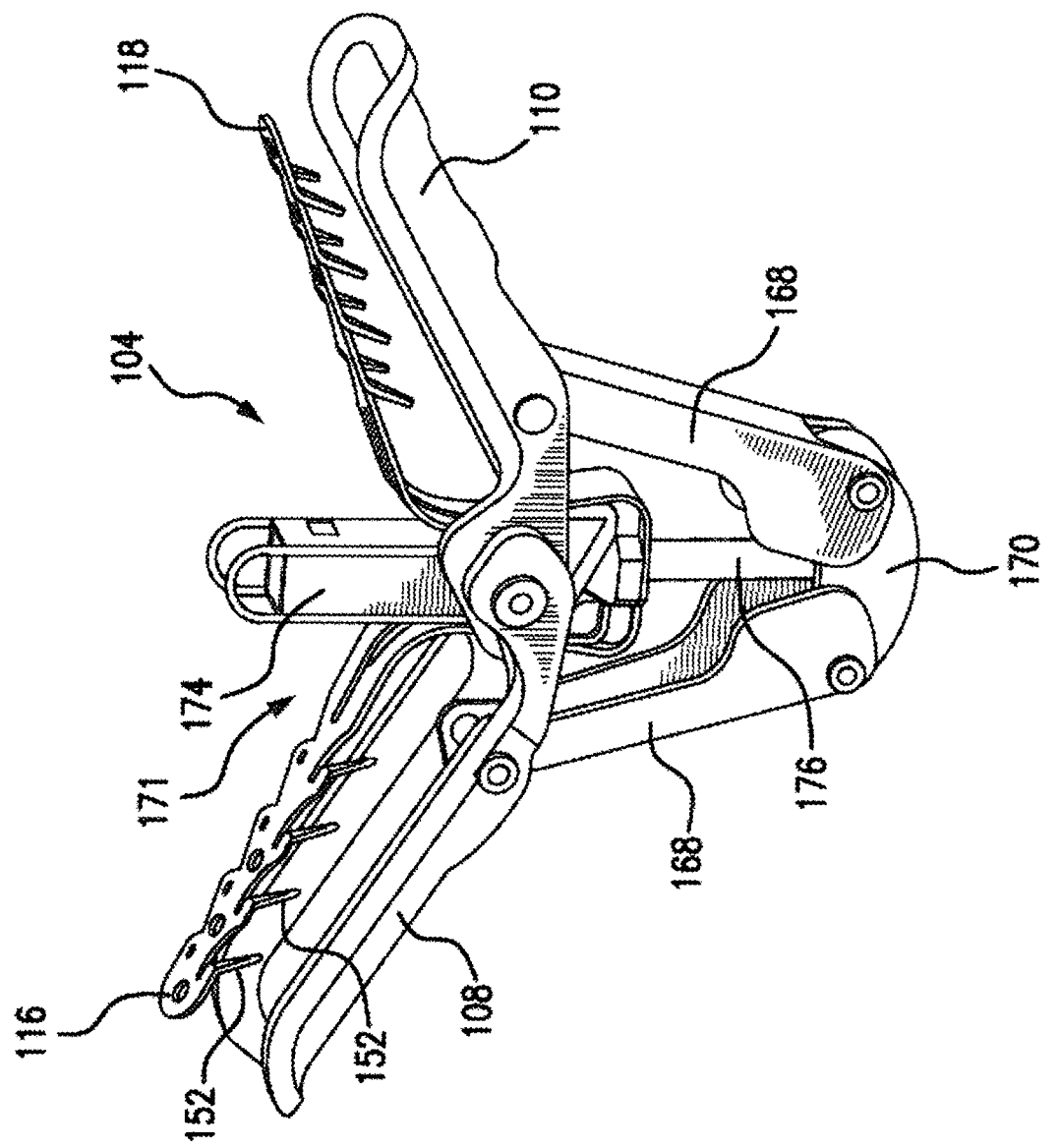
FIG. 5 is a perspective view of an exemplary embodiment of a fixation device for use in accordance with the disclosed subject matter.
Figure 6:
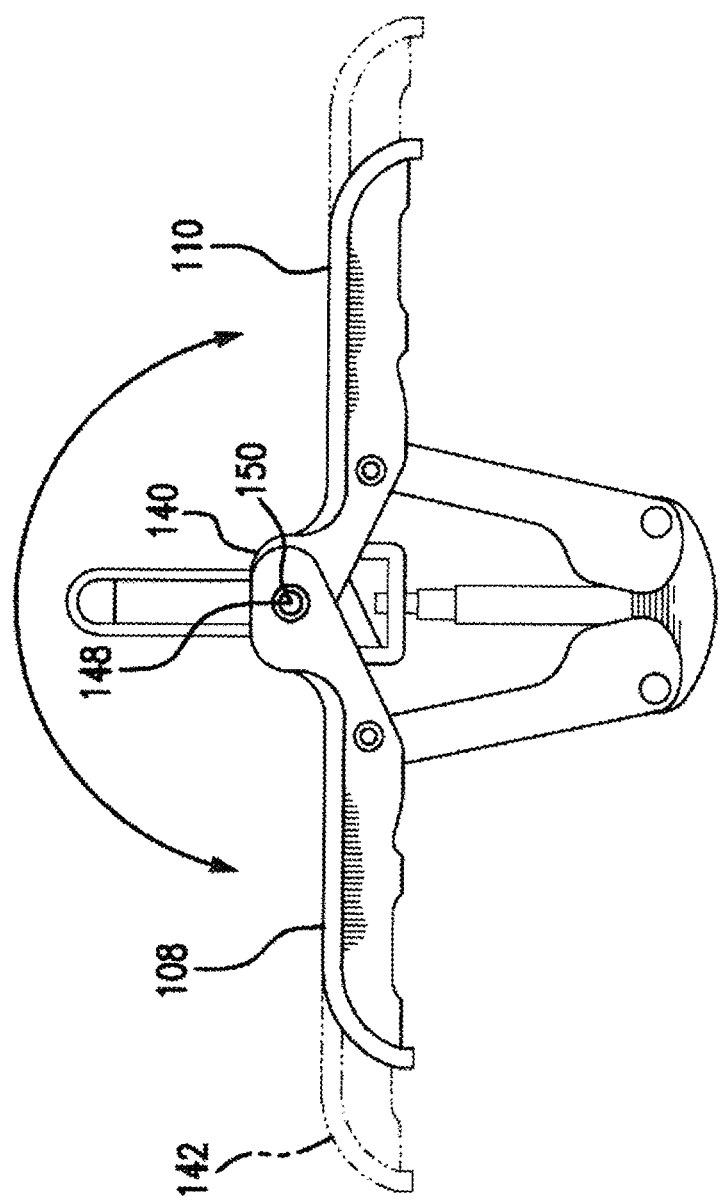
FIG. 6 is a front view of the fixation device of FIG. 5 at a different position, wherein optional arms of greater length are depicted in dashed lines.

Referring to FIGS. 5 and 6 for purpose illustration and not limitation, an exemplary fixation device 104 for fixation of native leaflets of a heart valve is disclosed herein. The fixation device as embodied herein can include a central assembly 171. The central assembly 171 can include various central components for operation and release of the fixation device 104 for example, a coupling member 174 as described in the disclosures of the patents and applications incorporated by reference herein. The fixation device as depicted can include at least one arm 108 moveably coupled to the central assembly 171. As shown, the fixation device can further include a second arm 110 moveably coupled to the central assembly 171.

With reference to FIG. 6, and further in accordance with the disclosed subject matter, each arm 108, 110 can be rotatable about a respective axis point 148, 150 between closed, open and inverted positions, as well as any position therebetween. Furthermore, the arms 108, 110 can be selected from a range of suitable lengths, wherein the appropriate length can be selected by the physician or health care provided, for example after inspection of a patient. For purpose of comparison, a first length of each arm 108, 110 is depicted in FIG. 6 in solid lines, and a second longer length of each arm of the disclosed subject matter is depicted in dashed lines. The arms in solid lines can be an entirely separate arm with a different length as compared to the arm in dashed lines.

Figure 7A:
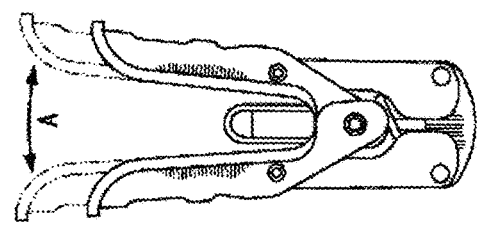
FIG. 7A-7C are front views of the fixation device of FIG. 5 at various positions, wherein optional arms of greater length are depicted with dashed lines.
Figure 7B:
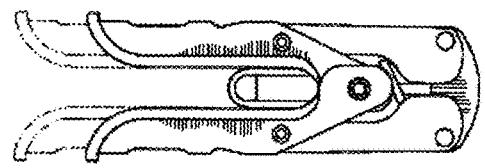
Figure 7C:
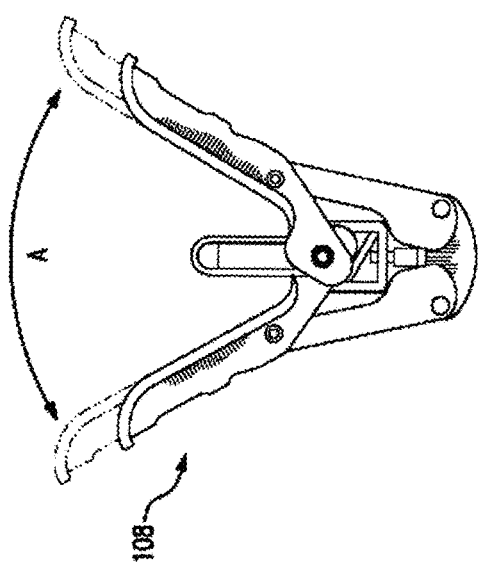

As depicted herein in FIGS. 7A-7C, various positions of the fixation device 104 are depicted for purpose of illustration and not limitation. Elongated arms are illustrated in dashed lines for comparison to shorter arms (in solid lines). In FIG. 7A, the fixation device is in the closed position, wherein the arms are positioned axially in alignment, e.g., vertically or nearly vertically as shown. FIGS. 7B and 7C illustrate the arms positioned with an angle A between each other. In FIG. 7B, angle A is about 10 degrees, and in FIG. 7C, angle A is about 60 degrees. As disclosed herein, the fixation device is in the closed position when angle A is about 30 or less degrees. Although not depicted, the arms can continue to open until angle A exceeds 180 degrees, e.g., inverted.

The fixation device 104 can further include at least one gripping element 116 moveable relative to the at least one arm 108 to capture native leaflet therebetween. In accordance with the disclosed subject matter, each arm can be configured to define or have a trough aligned along the longitudinal axis. The trough can have a width sized greater than a width of the gripper element so as to receive the gripper element therein.

The fixation device can further include a second gripping element 118 moveable relative to the second arm 110 to capture a second native leaflet therebetween. Further, in accordance with the disclosed subject matter, the at least one gripping element 116, 118 can have at least one friction element 152 along a length thereof. As embodied herein, each gripping element 116, 118 can include a plurality of friction elements 152, which can be disposed in rows. For example, each gripping element 116 and 118 can have a least four rows of friction elements 152. The friction elements 152 can allow for improved tissue engagement during leaflet capture. This gripping element design can increase the assurance that single device leaflet detachment will not occur during or after a procedure. To adjust the fixation device after an initial leaflet capture, the arms can be opened, the gripping element can be raised vertically, and issue can disengage from the fixation device, facilitating re-grasp and capture.

As further embodied herein, each gripping element 116, 118 can be biased toward each respective arm 108, 110. Prior to leaflet capture, each gripping element 116, 118 can be moved inwardly toward a longitudinal center of the device (e.g., away from each respective arm 108, 110) and held with the aid of one or more gripper element lines (not shown), which can be in the form of sutures, wire, nitinol wires, rods, cables, polymeric lines, or other suitable structures. The sutures can be operatively connected with the gripping elements 116, 118 in a variety of ways, such as by being threaded though loops disposed on gripping elements 116, 118.

Fixation device 104 can further include two link members or legs 168, and as embodied herein, each leg 168 has a first end rotatably joined with one of the arms 108, 110 and a second end rotatably joined with a base 170. The base 170 can be operatively connected with a stud 176 which can be operatively attached to an actuator rod 64 of the delivery system (see FIG. 9). In some embodiments, the stud 176 can be threaded such that the actuator rod 64 can attach to the stud 176 by a screw-type action. Further, the connection point between the stud 176 and the actuator rod 64 can be disposed within the coupling member 174. However, the actuator rod 64 and stud 176 can be operatively connected by any mechanism which is releasable to allow the fixation device 104 to be detached. The stud 176 can be axially extendable and retractable to move the base and therefore the legs 168, which can rotate the arms 108, 110 between closed, open and inverted positions. Immobilization of the stud, such as by a locking mechanism, can hold the legs 168 in place and therefore lock the arms 108, 110 in a desired position. Further details are disclosed in the patents and published applications incorporated by reference herein.

As previously noted, a native leaflet can be captured between each arm and respective gripping element. Each arm can then be moved toward its closed position. In this matter, adjacent leaflets can further be captured between the arms in the closed position. For example, and for illustration only, FIGS. 8A-8B show the fixation device 104 depicted with arms 108, 110 at an angle A of about 10 to 30 degrees with two leaflets captured therebetween, wherein each leaflet is captured between an arm and a respective gripping element (gripping elements not shown). As illustrated in FIG. 8B, a contact patch area 222 depicted in dashed lines and is defined by the area of tissue captured between the arms. The contact patch area 222 can depict a tissue-to-tissue contact patch area defined by area of a leaflet in contact with a counterpart leaflet. As previously noted, FIG. 8B depicts the contact patch area 222 when the fixation device is oriented at angle A of about 10 to 30 degrees.

Figure 9:
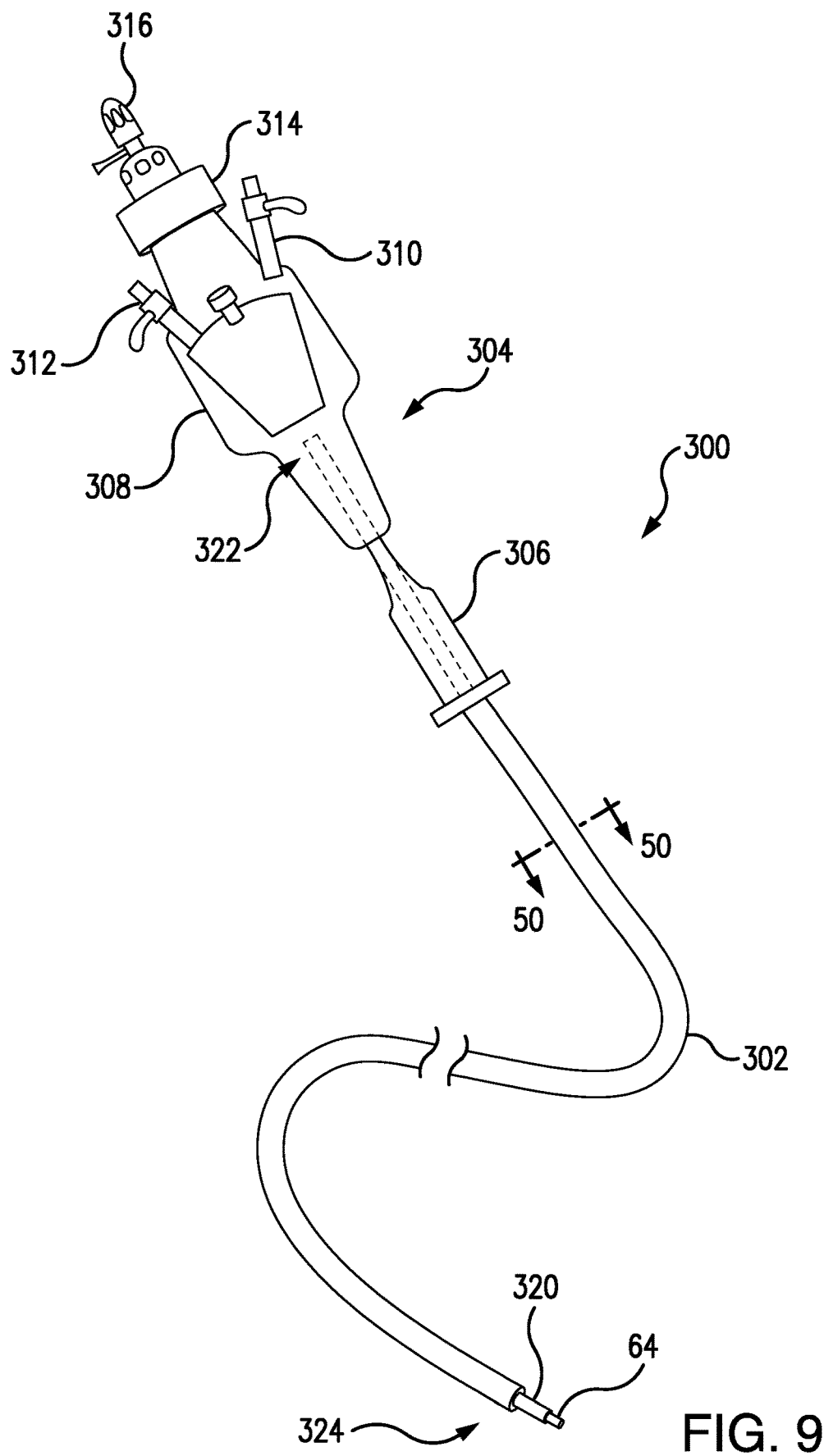
FIG. 9 is a perspective view of an exemplary embodiment of a delivery device for use in accordance with the disclosed subject matter.

Referring to FIG. 9 for purpose of illustration and not limitation, an exemplary delivery device 300 is provided for delivery of a fixation device as disclosed. That is, the delivery device 300 can be used to introduce and position a fixation device as described above. The delivery device 300 can include a shaft 302, having a proximal end 322 and a distal end 324, and a handle 304 attached to the proximal end 322. A fixation device (not shown) can be removably couple-able to the distal end 324 for delivery to a site within the body, for example, the mitral valve. Thus, extending from the distal end 324 is a coupling structure 320 for coupling with a fixation device 104. Also extending from the distal end 324 is an actuator rod 64. The actuator rod 64 is connectable with the fixation device 104 and can act to manipulate the fixation device 104, for example, opening and closing the arms 108, 110. Handle 304 of the delivery device 300 is shown, including main body 308, proximal element line handle 312, the lock line handle 310, the actuator rod control 314 and the actuator rod handle 316, among other features. The handle 304 is supported by the support base 306 which is connected to handle 1057.

Figure 10:
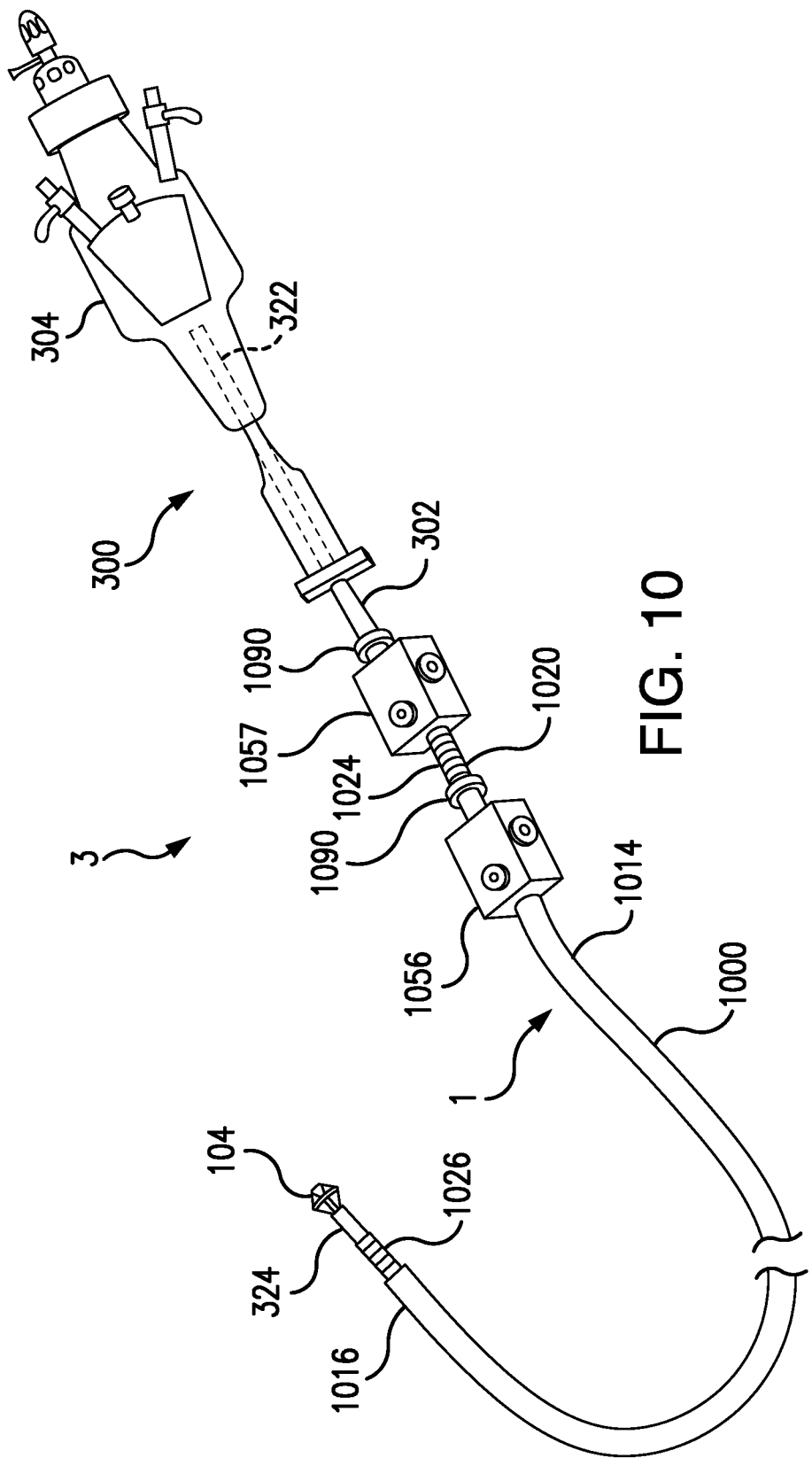
FIG. 10 is a perspective view of an exemplary embodiment of a delivery system including a delivery device and steerable guide system in accordance with the disclosed subject matter.

Referring to FIG. 10, for purpose of illustration and not limitation, medical delivery system 3 including a steerable guide system 1 is provided. The steerable guide system 1 can include multiple steerable catheter components. For example, and not limitation, steerable guide system 1 can include an outer guide catheter 1000, having a proximal end 1014 and a distal end 1016, and an inner guide catheter 1020, having a proximal end 1024 and a distal end 1026, wherein the inner guide catheter 1020 is positioned coaxially within the outer guide catheter 1000, as shown. In addition, a hemostatic valve 1090 can be disposed within handle 1056 or external to handle 1056 as shown to provide leak-free sealing with or without the inner guide catheter 1020 in place. The distal ends 1016, 1026 of catheter 1000, 1020, respectively, are sized to be passable to a body cavity, typically through a body lumen such as a vascular lumen.

Manipulation of the guide catheter 1000, 1020 can be achieved with the use of handles 1056, 1057 attached to the proximal ends of the catheter 1000, 1020. As shown, handle 1056 is attached to the proximal end 1014 of outer guide catheter 1000 and handle 1057 is attached to the proximal end 1024 of inner guide catheter 1020. Inner guide catheter 1020 is inserted through handle 1056 and is positioned coaxially within outer guide catheter 1000.

The delivery catheter 300 can be inserted though handle 1057 and can be positioned coaxially within inner guide catheter 1020 and outer guide catheter 1000. The delivery catheter 300 includes a shaft 302, having a proximal end 322 and a distal end 324, and a handle 304 attached to the proximal end 322. A fixation device 104 can be removably coupled to the distal end 324 for deliver to a site within the patient The outer guide catheter 1000 and/or the inner guide catheter 1020 can be precurved and/or have steering mechanisms to position the distal ends 1016, 1026 in desired directions. Precurvature or steering of the outer guide catheter 1000 can direct the distal end 1016 in a first direction to create a primary curve while precurvature and/or steering of the inner guide catheter 1020 can direct distal end 1026 in a second direction, different from the first, to create a secondary curve. Together, the primary and secondary curves can form a compound curve. Furthermore, advancement of the entire interventional system 3 or the inner guide catheter 1020 (relative to the outer guide catheter 1000) can further direct the distal end 1026 of the inner guide catheter 1020 toward a desired position. Advancement of the delivery catheter 300 through the coaxial guide catheters 1000, 1020 can guide the delivery catheter 300 through the compound curve toward a desired direction, usually in a direction which will position the fixation device 104 in a desired location in the body.

Figure 11:
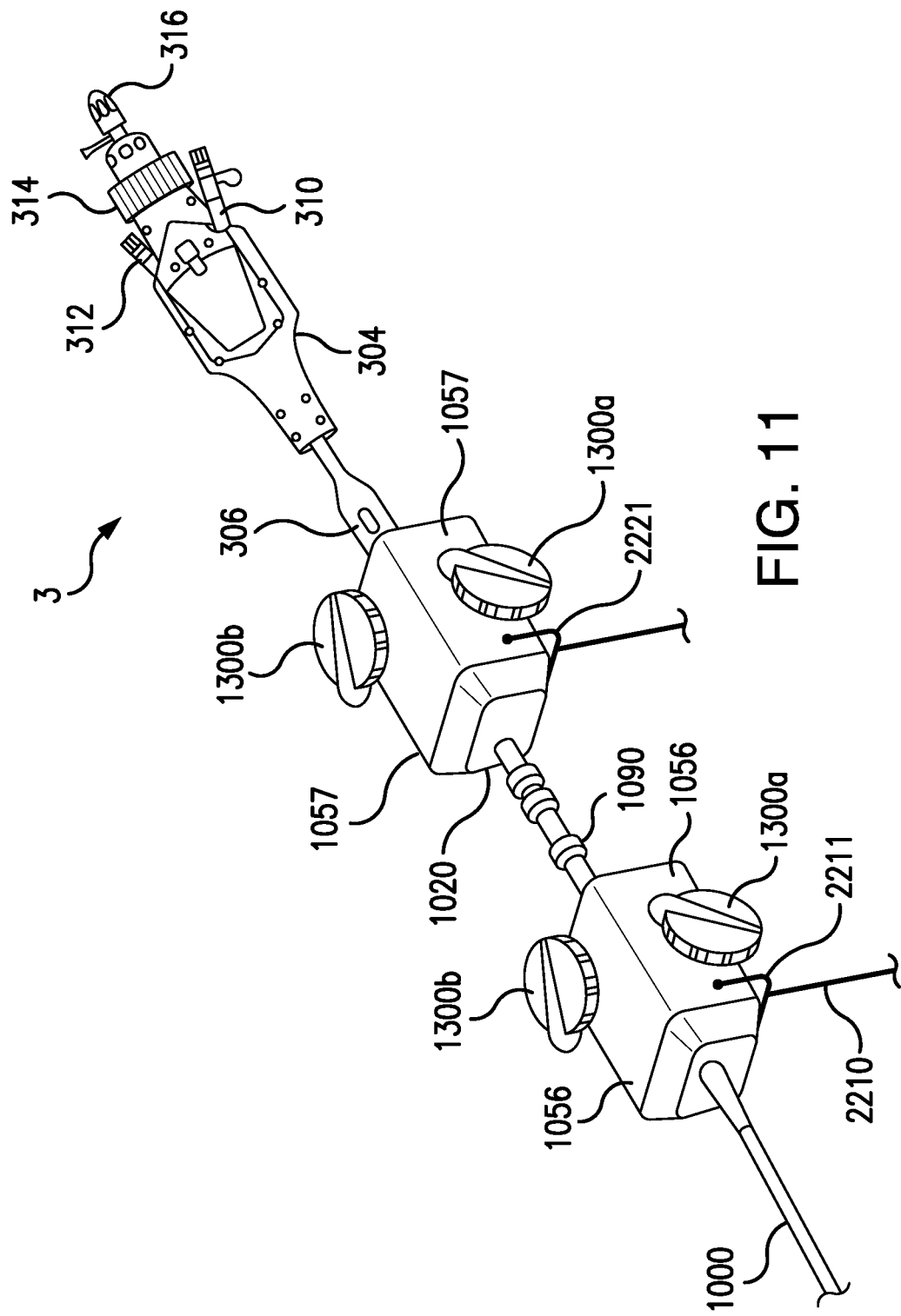
FIG. 11 is an enlarged perspective view of a portion of the exemplary embodiment of a delivery system of FIG. 10, depicting steering knobs for manipulation of the steerable guide catheters in accordance with the disclosed subject matter.

FIG. 11 is an enlarged view of the controls of a medical delivery system 3 in accordance with the disclosed subject matter. Handles 1056, 1057 of the steerable guide system 1 are shown. Each handle 1056, 1057 includes a set of steering knobs 1300a, 1300b, as shown. Manipulation of guide catheter 1000 and 1020 can be achieved with the use of the steering knobs 1300a, 1300b attached to the proximal ends of the catheters 1000, 1020. Further details of exemplary delivery systems are disclosed in the patents and published applications incorporated by reference herein. Alternative handles and/or controls likewise are contemplated in accordance with the disclosed subject matter. Distal arm 2210, distal attachment 2211 and proximal attachment 2221 of stabilizer 2000 are shown schematically in FIG. 11. Particularly, distal attachment 2211 can receive handle 1056 and proximal attachment 2221 can receive handle 1057.

In accordance with the disclosed subject matter, the fixation device 104 can be adapted for repair of a heart valve, such as a mitral valve, using an antegrade approach from a patient's left atrium. The fixation device 104 can be introduced in a femoral vein of a patient and advanced through the inferior vena cava into the heart and, for mitral valve repair, across a penetration in the interatrial septum. The fixation device 104 can be advanced through the mitral valve from the left atrium to the left ventricle. The arms 108, 110 can be oriented to be perpendicular to a line of coaptation and positioned with the arms 108, 110 contacting the ventricular surface of the valve leaflets, thereby grasping the leaflets. The gripping elements 116, 118 can remain on the atrial side of the valve leaflets with the leaflets disposed between the gripping elements 116, 118 and the arms 108, 110. The fixation device 104 can be manipulated as desired to reposition the device such that the leaflets are properly grasped at a desired location. Repositioning can be performed with the fixation device 104 in the open position. As embodied herein, regurgitation of the valve can also be checked while the fixation device 104 is in the open position. If regurgitation is not satisfactorily reduced, the fixation device 104 can be repositioned and regurgitation checked again until the desired results are achieved.

With reference to FIGS. 1-4 and 9-11 for purpose of illustration and not limitation, during use, stabilizer 2000 can support delivery system 3. Distal attachment 2211 can receive (and support) handle 1056 coupled to the proximal end 1014 of outer guide catheter 1000. Proximal attachment 2221 can receive (and support) handle 1057 coupled to the proximal end 1024 of inner guide catheter 1020 as well as handle 304 coupled to the proximal end 322 of delivery catheter 300. During a mitral valve repair procedure, for example, the distal end 1016 of the outer guide catheter 1000 can be advanced through a blood vessels of the patient (for example the femoral vein and inferior vena cava) to the right atrium of the heart, across the septum, and into the left atrium of the heart. Once the distal end 1016 of the outer guide catheter 1000 is placed in the left atrium, handle 1056 can then be coupled to distal attachment 2211. The distal end 1026 of inner guide catheter 1020 together with the distal end 324 of delivery catheter 300 and fixation device 104 coupled thereto, can be advanced through the outer guide catheter 1000 to left atrium of the heart. Once the distal end 1026 of the inner guide catheter 1020 is advance to the left atrium, handle 1057 can be coupled to proximal attachment 2221. Marker 2222 can assist the user in initially positioning the tip of the distal end 1026 of inner guide catheter 1020 (and therefore fixation device 104) relative to the outer guide catheter 1000. Once the fixation device 104 has been delivered to the left atrium, it can be positioned in the desired location using handles 1056, 1057 to steer the distal end of the delivery system 3 (as described above), advancing the entire delivery system relative the patient by operating sled drive mechanism 2230, and/or advancing the inner guide catheter (and delivery catheter 300 and fixation device 104) relative the outer guide catheter 1000 by operating attachment drive mechanism 2240.

Once the fixation device 104 has been positioned in a desired location relative to the valve leaflets, the leaflets can then be captured between the gripping elements 116, 118 and the arms 108, 110. As embodied herein, the gripping elements 116, 118 can be lowered toward the arms 108, 110 to dispose the leaflets therebetween. The arms 108, 110 can be closed to an angle selectable by the user and locked to the prevent the arms 108, 110 from moving toward an open position. The fixation device 104 can then be detached from the distal end of the delivery catheter 300. After detachment, the repair of the leaflets or tissue can be observed by non-invasive visualization techniques, such as echocardiography, to ensure the desired outcome. If the repair is not desired, the fixation device 14 can be retrieved. If the repair is satisfactory, the gripper element lines can be disconnected, and the fixation device can be released for implantation.

In view of the above and in accordance with the disclosed subject matter, a system is provided including an outer guide catheter, an inner guide catheter, an outer-guide-catheter handle, an inner-guide-catheter handle, and a stabilizer. The outer guide catheter includes a distal end portion and a proximal end portion, and the inner guide catheter includes a distal end portion and a proximal end portion. The outer-guide-catheter handle is coupled to the proximal end portion of the outer guide catheter and the inner-guide catheter handle is coupled to the proximal end portion of the inner guide catheter. The stabilizer includes a base and a sled coupled to the base. The sled includes an outer-guide-catheter arm including an outer-guide-catheter attachment for receiving the outer-guide-catheter handle, and an inner-guide-catheter arm including an inner-guide-catheter attachment for receiving the inner-guide-catheter handle. The sled is translatable relative to the base and the inner-guide-catheter attachment is translatable relative to the inner-guide-catheter arm. Additional features as described above can be incorporated in the system.

While the embodiments disclosed herein utilize a push-to-open, pull-to-close mechanism for opening and closing arms it should be understood that other suitable mechanisms can be used, such as a pull-to-open, push-to-close mechanism. A closure bias can be included, for example using a compliant mechanism such as a linear spring, helical spring, or leaf spring. Other actuation elements can be used for deployment of the gripper elements.

While the disclosed subject matter is described herein in terms of certain preferred embodiments for purpose of illustration and not limitation, those skilled in the art will recognize that various modifications and improvements can be made to the disclosed subject matter without departing from the scope thereof. Moreover, although individual features of one embodiment of the disclosed subject matter can be discussed herein or shown in the drawings of one embodiment and not in other embodiments, it should be readily apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A medical delivery system, comprising:
   a steerable guide system having a first portion and a second portion; and a stabilizer having a base portion, a distal arm, and a proximal arm, the distal arm extending from a distal portion of the base portion and having a distal attachment configured to receive the first portion of the steerable guide system, and the proximal arm extending from a proximal portion of the base portion and having a proximal attachment, the proximal attachment having opposed first and second side walls and opposed first and second end walls, the side walls and end walls intersecting one another to define an upper surface of the proximal attachment and an elongate recess extending through the upper surface toward the base portion, the elongate recess being configured to receive the second portion of the steerable guide system and being bounded on all sides by the first and second end walls and first and second side walls, wherein, when the second portion of the steerable guide system is lowered into and received by the elongate recess and the first portion is attached to the distal attachment, the second portion of the steerable guide system is translatable in a proximal-distal direction relative to the first portion of the steerable guide system and the base portion.

2. The medical delivery system of claim 1, wherein the elongate recess has a rectangular shape with a longitudinal axis extending from the first end wall to the second end wall.

3. The medical delivery system of claim 2, wherein the longitudinal axis of the elongate recess extends at an oblique angle relative to a longitudinal axis of the base portion.

4. The medical delivery system of claim 1, wherein the first and second side walls and first and second ends walls are flush such that the upper surface defines a plane extending at an oblique angle relative to a longitudinal axis of the base portion.

5. The medical delivery system of claim 1, wherein the upper surface defines an upper side of the proximal attachment opposite a lower side of the proximal attachment, the lower side of the proximal attachment having a proximal leg and a distal leg extending in a direction away from the upper surface.

6. The medical delivery system of claim 5, wherein the stabilizer further includes a leadscrew attached to the proximal attachment and the proximal arm, the leadscrew extending through the proximal and distal legs of the proximal attachment and being operable to translate the proximal attachment relative to the proximal arm.

7. The medical delivery system of claim 1, wherein the proximal attachment is translatable relative to the proximal arm.

8. The medical delivery system of claim 7, wherein the proximal attachment is translatable relative to the proximal arm with and without the second portion of the steerable guide system being coupled to the proximal attachment.

9. The medical delivery system of claim 1, wherein the proximal arm includes first and second arms defining a channel therebetween, and the proximal attachment is positioned within and translatable along the channel.

10. The medical delivery system of claim 9, wherein the proximal attachment is attached to the first and second arms via a leadscrew.

11. The medical delivery system of claim 10, wherein the leadscrew extends through the first and second end walls of the proximal attachment.

12. The medical delivery system of claim 1, wherein the first portion of the steerable guide system includes an outer guide catheter and an outer-guide-catheter handle coupled to a proximal end portion of the outer guide catheter, and the second portion of the steerable guide system includes an inner guide catheter and an inner-guide-catheter handle coupled to a proximal end portion of the inner guide catheter.

13. The medical delivery system of claim 12, wherein the elongate recess is configured to receive a least a portion of the inner-guide-catheter handle.

14. The medical delivery system of claim 12, further comprising a delivery catheter, a delivery catheter handle, and a fixation device, the delivery catheter having a distal end portion and a proximal end portion, the delivery device being releasably coupled to the distal end portion of the delivery catheter, and the delivery-catheter handle being coupled to the proximal end portion of the delivery catheter and configured to operate and release the fixation device from the delivery catheter, the distal end of the delivery catheter and the fixation device being passable through the inner-guide-catheter handle and the inner guide catheter.

15. The medical delivery system of claim 1, wherein the base portion includes a base, a sled, and sled drive mechanism coupled to the base and the sled, the sled being translatable relative to the base via operation of the sled drive mechanism.

16. The medical delivery system of claim 15, wherein the sled drive mechanism includes a leadscrew.

17. A medical delivery system, comprising:
a steerable guide system having a first portion and a second portion; and
a stabilizer comprising:
a base portion having a proximal portion and a distal portion,
a distal member extending from the distal portion of the base portion and being configured to attach to the first portion of the steerable guide system, and
a proximal member extending from the proximal portion of the base portion and having first and second side walls and first and second end walls bounding an elongate recess such that the first and second side walls form respective lateral boundaries and the first and second end walls form respective proximal and distal boundaries of the elongate recess, the elongate recess having a longitudinal axis extending from the first end wall to the second end wall and being inclined toward the distal portion of the base portion,
wherein, when the second portion of the steerable guide system is lowered into and received by the elongate recess of the proximal member and the first portion of the steerable guide catheter is attached to the distal member, the second portion of the steerable guide system is translatable in a direction parallel to or coaxial with the longitudinal axis of the proximal member and relative to the first portion of the steerable guide system and the base portion.

18. The medical delivery system of claim 17, wherein the elongate recess has a rectangular shape.

19. The medical delivery system of claim 17, wherein the first and second side walls and first and second ends walls define a planar upper surface, the elongate recess extending through the upper surface.

20. The medical delivery system of claim 17, wherein the proximal member includes a proximal arm defining a channel and a proximal attachment slidably disposed within the channel, the proximal attachment having the elongate recess such that sliding the proximal attachment correspondingly moves the elongate recess and the second portion of the steerable guide system disposed therein.

21. The medical delivery system of claim 17, wherein the first portion of the steerable guide system includes an outer guide catheter and an outer-guide-catheter handle coupled to a proximal end portion of the outer guide catheter, and the second portion of the steerable guide system includes an inner guide catheter and an inner-guide-catheter handle coupled to a proximal end portion of the inner guide catheter.

22. A medical delivery system, comprising:
a steerable guide system having a first portion and a second portion; and
a stabilizer having a base portion, a distal arm, and a proximal arm, the distal arm extending from a distal portion of the base portion and having a distal attachment configured to receive the first portion of the steerable guide system, the proximal arm extending from a proximal portion of the base portion and having a proximal attachment, the proximal attachment having opposed first and second side walls, opposed first and second end walls, and an elongate recess extending between the first and second side walls and first and second end walls, the side walls and end walls intersecting one another to define a continuous upper surface extending about the elongate recess, wherein, when the second portion of the steerable guide system is lowered into and received by the elongate recess and the first portion is attached to the distal attachment, the second portion of the steerable guide system is translatable in a proximal-distal direction relative to the first portion of the steerable guide system and the base portion.

23. The medical delivery system of claim 22, wherein the elongate recess has a rectangular shape with a longitudinal axis extending from the first end wall to the second end wall.

24. The medical delivery system of claim 22, wherein the longitudinal axis of the elongate recess extends at an oblique angle relative to a longitudinal axis of the base portion.

25. The medical delivery system of claim 22, wherein the continuous upper surface is a planar surface.

26. The medical delivery system of claim 22, wherein the continuous upper surface defines an upper side of the proximal attachment opposite a lower side of the proximal attachment, the lower side of the proximal attachment having a proximal leg and a distal leg extending in a direction away from the continuous upper surface.

* * * * *